United States Patent
Yukumoto et al.

(10) Patent No.: US 9,782,720 B2
(45) Date of Patent: Oct. 10, 2017

(54) DEGRADANT CONCENTRATION MEASUREMENT DEVICE AND ACIDIC GAS REMOVAL DEVICE

(71) Applicant: MITSUBISHI HEAVY INDUSTRIES, LTD., Tokyo (JP)

(72) Inventors: Atsuhiro Yukumoto, Tokyo (JP); Kouji Horizoe, Tokyo (JP); Yudai Kato, Tokyo (JP); Haruaki Hirayama, Tokyo (JP); Kazuo Ishida, Kanagawa (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 428 days.

(21) Appl. No.: 14/370,891

(22) PCT Filed: Feb. 8, 2013

(86) PCT No.: PCT/JP2013/053138
§ 371 (c)(1),
(2) Date: Jul. 7, 2014

(87) PCT Pub. No.: WO2013/132962
PCT Pub. Date: Sep. 12, 2013

(65) Prior Publication Data
US 2015/0044100 A1    Feb. 12, 2015

(30) Foreign Application Priority Data

Mar. 9, 2012 (JP) .................... 2012-053788

(51) Int. Cl.
*B01D 53/34* (2006.01)
*B01D 53/82* (2006.01)
(Continued)

(52) U.S. Cl.
CPC ....... *B01D 53/346* (2013.01); *B01D 53/1425* (2013.01); *B01D 53/1475* (2013.01);
(Continued)

(58) Field of Classification Search
CPC .. B01D 2252/20478; B01D 2258/0283; B01D 53/1425; B01D 53/1475;
(Continued)

(56) References Cited

U.S. PATENT DOCUMENTS 6,544,492 B1 * 4/2003 DeBerry ............ B01D 53/1418
423/228
8,480,795 B2 * 7/2013 Siskin .................... B01D 3/143
95/235

(Continued)

FOREIGN PATENT DOCUMENTS

CN    1088472 A    6/1994
CN    1380973 A    11/2002
(Continued)

OTHER PUBLICATIONS

Decision of a Patent Grant dated Dec. 8, 2015, issued in counterpart Japanese patent application No. 2012053788, with English translation. (3 pages).
(Continued)

*Primary Examiner* — Amber R Orlando
*Assistant Examiner* — Cabrena Holecek
(74) *Attorney, Agent, or Firm* — Westerman, Hattori, Daniels & Adrian, LLP

(57) ABSTRACT

A degradant concentration measurement device 14 according to the invention has an electric conductivity measurement instrument 71A measuring the electric conductivity of a lean solution 16 that is an acidic gas-absorbing solution and detection means 72 obtaining the concentration of a degradant contained in a lean solution 16 from the measured electric conductivity of the lean solution 16 based on the relationship between the previously-obtained electric conductivity of the lean solution 16 and the concentration of the degradant contained in the lean solution 16.

12 Claims, 6 Drawing Sheets

(51) Int. Cl.
| | |
|---|---|
| *G01N 27/02* | (2006.01) |
| *G01N 33/00* | (2006.01) |
| *G01N 27/06* | (2006.01) |
| *B01D 53/14* | (2006.01) |
| *C10K 1/00* | (2006.01) |
| *C10K 1/10* | (2006.01) |
| *C10L 3/10* | (2006.01) |

(52) U.S. Cl.
CPC .............. *B01D 53/82* (2013.01); *C10K 1/003* (2013.01); *C10K 1/10* (2013.01); *G01N 27/02* (2013.01); *G01N 27/06* (2013.01); *G01N 33/0027* (2013.01); *B01D 2252/20478* (2013.01); *B01D 2258/0283* (2013.01); *C10L 3/102* (2013.01); *C10L 2290/541* (2013.01); *C10L 2290/60* (2013.01); *Y02C 10/06* (2013.01); *Y02P 20/152* (2015.11)

(58) Field of Classification Search
CPC ...... B01D 53/346; B01D 53/82; C10K 1/003; C10K 1/10; C10L 2290/541; C10L 2290/60; C10L 3/102; G01N 27/02; G01N 27/06; G01N 33/0027; Y02C 10/06; Y02P 20/152
See application file for complete search history.

(56) References Cited

U.S. PATENT DOCUMENTS

| | | |
|---|---|---|
| 2008/0223215 A1 | 9/2008 | Iijima et al. |
| 2012/0285326 A1 | 11/2012 | Ito et al. |

FOREIGN PATENT DOCUMENTS

| | | |
|---|---|---|
| CN | 1439874 A | 9/2003 |
| CN | 101612512 A | 12/2009 |
| CN | 101721883 A | 6/2010 |
| CN | 201558659 U | 8/2010 |
| CN | 102133499 A | 7/2011 |
| CN | 102343201 A | 2/2012 |
| JP | 55-27083 A | 2/1980 |
| JP | 5-256835 A | 10/1993 |
| JP | 6-40081 B2 | 5/1994 |
| JP | 8-89756 A | 4/1996 |
| JP | 11-244649 A | 9/1999 |
| JP | 2003-93835 A | 4/2003 |
| JP | 2003-94063 A | 4/2003 |
| JP | 3401387 B2 | 4/2003 |
| JP | 3518112 B2 | 4/2004 |
| JP | 2005-240588 A | 9/2005 |
| JP | 2006-212526 A | 8/2006 |
| JP | 3990601 B2 | 10/2007 |
| JP | 4104105 B2 | 6/2008 |
| JP | 2008-221166 A | 9/2008 |
| JP | 4377104 B2 | 12/2009 |
| JP | 2010-132602 A | 6/2010 |
| JP | 2011-63535 A | 3/2011 |
| JP | 4750279 B2 | 8/2011 |
| JP | 2011-177615 A | 9/2011 |
| JP | 2012-149018 A | 8/2012 |
| WO | 2011/104919 A1 | 9/2011 |

OTHER PUBLICATIONS

Notice of Acceptance dated Dec. 3, 2015, issued in counterpart Australian patent application No. 2013228777. (4 pages).
Notice of Allowance dated Jun. 24, 2016, issued in counterpart Korean Patent Application No. 10-2014-7021584, with Partial English translation. (4 pages).
International Search Report dated May 14, 2013 issued in corresponding application No. PCT/JP2013/053138.
Office Action dated Aug. 24, 2015, issued in counterpart Chinese Patent Application No. 201380011183.0 w/English translation (30 pages).
Translation of Written Opinion of the Searching Authority dated May 14, 2013 issued in corresponding Application No. PCT/JP2013/053138.

* cited by examiner

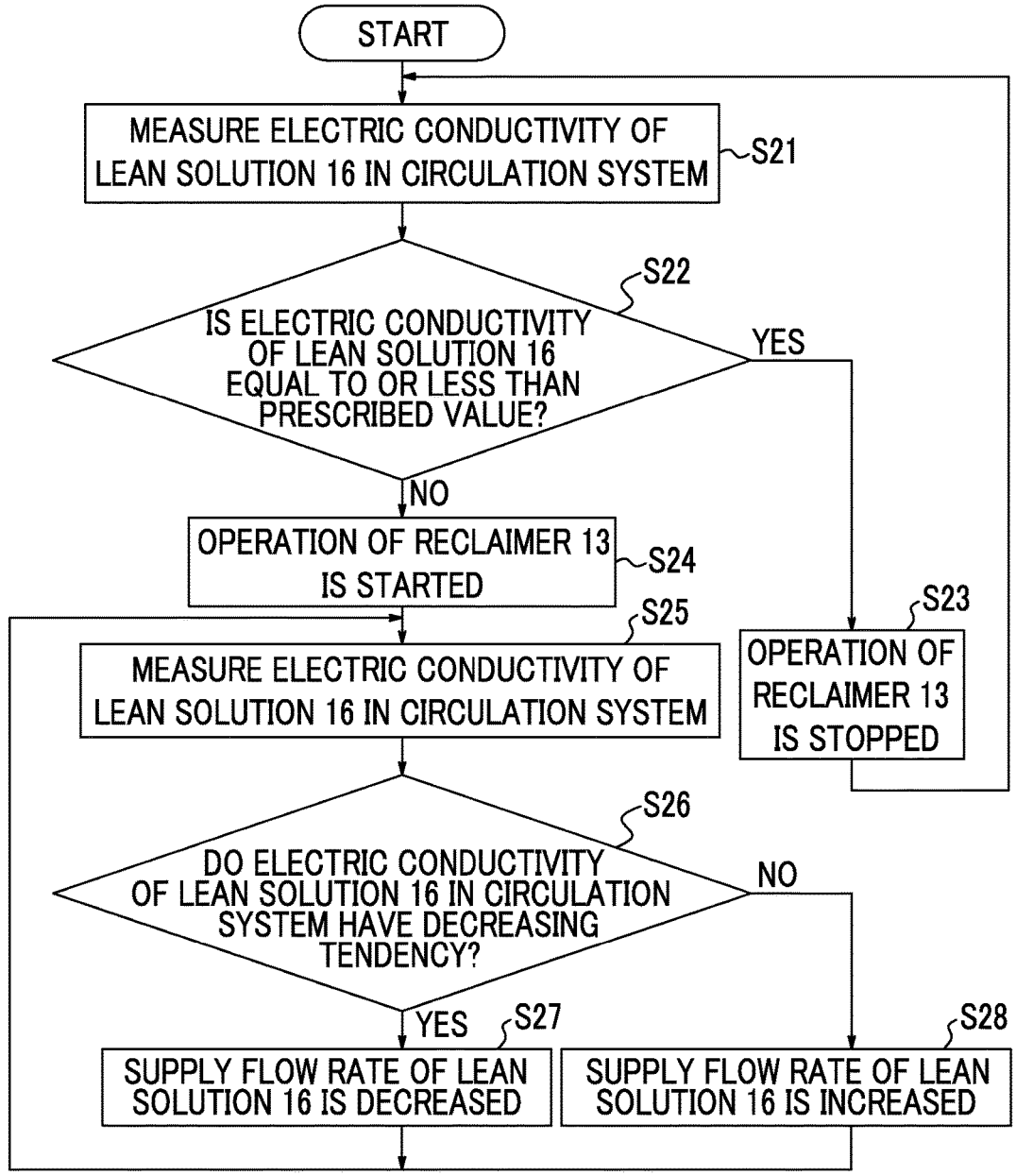

DEGRADANT CONCENTRATION MEASUREMENT DEVICE AND ACIDIC GAS REMOVAL DEVICE

TECHNICAL FIELD

The present invention relates to a degradant concentration measurement device and an acidic gas removal device that can be used to measure and manage a degradant contained in an absorbing solution used to remove acidic components (for example, carbon dioxide ($CO_2$), hydrogen sulfide ($H_2S$) and the like) contained in gas.

BACKGROUND ART

In a thermal power plant or the like in which a large amount of a fossil fuel is used, exhaust gas generated due to the combustion of a fossil fuel in a boiler, coal gasified gas (gasified gas) obtained by gasifying coal, and natural gas contain acidic gas components (for example, $H_2S$, $CO_2$ and the like). Gas containing the above-described acidic components is brought into gas-liquid contact with an amine-based acidic gas-absorbing solution in an absorption tower so that acidic gas is absorbed in the acidic gas-absorbing solution, whereby the acidic gas in the gas is removed and recovered.

For example, a method is used in which an acidic gas-absorbing solution absorbs and removes acidic gas in gas such as exhaust gas and gasified gas in the absorption tower, then, the acidic gas absorbed in the acid gas-absorbing solution is released in a regeneration tower, the regenerated acidic gas-absorbing solution is resupplied to the absorption tower and reused, and the acidic gas-absorbing solution is circulated into a circulation system between the absorption tower and the regeneration tower, and used (for example, refer to PTL 1 and 2).

In a step of recovering the acidic gas component (for example, $CO_2$, $SO_2$ and the like) from exhaust gas exhausted from a boiler and a step of removing acidic gas components ($H_2S$, $CO_2$) in natural gas or coal gasified gas exhausted from a gasification furnace or the like, the amine-based acidic gas-absorbing solution being used generates a degradant called heat stable amine salt (HSAS) due to the degradation reaction of treatment gas components or decomposition of the acidic gas-absorbing solution.

Since a degradant generated due to the acidic gas-absorbing solution is highly corrosive, it is necessary to manage the degradant below the management concentration. As a method for managing the concentration of the degradant contained in the acidic gas-absorbing solution, for example, a method in which, when the concentration of a degradant in an acidic gas-absorbing solution circulating in the circulation system exceeds a prescribed value, the full amount of a degradant-absorbing solution in the circulation system is extracted and exchanged with a new absorbing solution, a method in which, while continuously carrying out an operation in the circulation system, some of an acidic gas-absorbing solution extracted from the circulation system is supplied to a reclaimer so as to remove a degradant in the acidic gas-absorbing solution, and the acidic gas-absorbing solution is returned to the circulation system, and the like are carried out.

In a case in which the reclaimer is used, when the concentration of the degradant in the acidic gas-absorbing solution circulating in the circulation system exceeds a prescribed value, some of the acidic gas-absorbing solution circulating in the circulation system is extracted and supplied to the reclaimer, the degradant in the acidic gas-absorbing solution is removed in the reclaimer, and the acidic gas-absorbing solution is returned to the circulating system. As described above, in the related art, the concentration of the degradant in the acidic gas-absorbing solution circulating in the circulation system is directly measured, and the reclaimer is repeatedly operated depending on the concentration.

CITATION LIST

Patent Literature

[PTL 1] Japanese Unexamined Patent Application Publication No. 2008-221166

[PTL 2] Japanese Unexamined Patent Application Publication No. 2011-63535

SUMMARY OF INVENTION

Technical Problem

However, in the operation of the reclaimer in PTL 1 and 2, since the measurement of the concentration of the degradant in the acidic gas-absorbing solution is determined by an operator based on the measurement results, the efficiency of the measurement of the concentration of the degradant in the acidic gas-absorbing solution is poor such that the burden on the operator is large, and the measurement is not easily carried out. Therefore, it has been difficult to take a rapid action to manage the acidic gas-absorbing solution depending on the concentration of the degradant in the acidic gas-absorbing solution circulating in the circulation system.

Therefore, there has been a demand for the appearance of a degradant concentration measurement device in which the acidic gas-absorbing solution circulating in the circulation system is managed and a rapid action can be taken depending on the concentration of the degradant in the acidic gas-absorbing solution circulating in the circulation system so that the burden of measuring the concentration of the degradant of the acidic gas-absorbing solution is reduced, and the concentration of the degradant in the acidic gas-absorbing solution can be efficiently and easily measured.

The invention has been made in consideration of the above-described problems, and an object of the invention is to provide a degradant concentration measurement device and an acidic gas removal device capable of reducing the burden of measuring the concentration of the degradant of the acidic gas-absorbing solution and of efficiently and easily measuring the concentration of the degradant in the acidic gas-absorbing solution.

Solution to Problem

A first invention of the invention for solving the above-described problems is a degradant concentration measurement device including electric conductivity measurement means for measuring an electric conductivity of an acidic gas-absorbing solution that absorbs an acidic gas component contained in supply gas to an acidic gas removal device, then, is regenerated, circulated again and used; and detection means for obtaining a concentration of a degradant contained in the acidic gas-absorbing solution from the measured electric conductivity of the acidic gas-absorbing solution based on a relationship between a previously-obtained electric conductivity of the acidic gas-absorbing solution and the concentration of the degradant contained in the acidic gas-absorbing solution.

A second invention is the degradant concentration measurement device according to the first invention, in which an ordinary-temperature-and-pressure state is formed through operations such as heat exchange and pressure adjustment as a pretreatment, and then the electric conductivity of the acidic gas-absorbing solution is measured.

A third invention is an acidic gas removal device including an absorption tower in which supply gas to the acidic gas removal device containing an acidic gas component is brought into contact with an acidic gas-absorbing solution so as to absorb and remove the acidic gas component; an absorbing solution-regeneration tower in which the acidic gas-absorbing solution absorbing the acidic gas component in the absorption tower is regenerated so as to produce a lean solution; and the degradant concentration measurement device according to the first or second invention in which a lean solution supply line supplying the lean solution to the absorption tower from the absorbing solution-regeneration tower is provided, an electric conductivity of the lean solution is measured, and a concentration of a degradant is detected.

A fourth invention is the acidic gas removal device according to the third invention, including a lean solution branching line that extracts some of the lean solution from the lean solution supply line; and a reclaimer that separates and removes a degradant in the lean solution extracted into the lean solution branching line by distillation or separates by distillation under reduced pressure using a boiling point difference.

A fifth invention is an acidic gas removal device including an absorption tower in which supply gas to the acidic gas removal device containing an acidic gas component is brought into contact with an acidic gas-absorbing solution so as to absorb and remove the acidic gas component; an absorbing solution-regeneration tower in which the acidic gas-absorbing solution absorbing the acidic gas component in the absorption tower is regenerated so as to produce a lean solution; a lean solution branching line that extracts some of the lean solution from the lean solution supply line; a reclaimer that separates by distillation or separates and removes a degradant in the lean solution extracted into the lean solution branching line by distillation under reduced pressure using a boiling point difference; a lean solution extraction line that extracts some of the lean solution in the reclaimer; a cooling device that is provided in the lean solution extraction line and cools the lean solution; and the degradant concentration measurement device according to the first or second invention that is provided in the lean solution extraction line and measures an electric conductivity of the cooled lean solution.

A sixth invention is the acidic gas removal device according to the fourth or fifth invention, including control means for controlling at least any one of starting and stopping of an operation of the reclaimer and a supply flow rate of the lean solution supplied to the reclaimer based on the electric conductivity of the lean solution measured in the degradant concentration measurement device.

A seventh invention is the acidic gas removal device according to the sixth invention, in which the control means determines whether or not the electric conductivity of the lean solution measured in the degradant concentration measurement device is equal to or less than a prescribed value so as to determine whether or not to start the operation of the reclaimer, and, after the starting of the operation of the reclaimer, determines whether or not the electric conductivity of the lean solution in the reclaimer measured in the degradant concentration measurement device is equal to or more than the prescribed value so as to determine the operation of the reclaimer.

An eighth invention is the acidic gas removal device according to the sixth invention, in which the control means determines whether or not the electric conductivity of the lean solution measured in the degradant concentration measurement device is equal to or less than a prescribed value so as to determine whether or not to start the operation of the reclaimer, and, after the starting of the operation of the reclaimer, determines whether or not the electric conductivity of the lean solution in the reclaimer measured in the degradant concentration measurement device has a decreasing tendency and adjusts the supply flow rate of the lean solution supplied to the reclaimer.

A ninth invention is the acidic gas removal device according to any one of the sixth to eighth inventions, in which the control means starts the operation of the reclaimer in a case in which the electric conductivity of the lean solution measured in the degradant concentration measurement device is in a range of 1 mS/cm to 30 mS/cm.

A tenth invention is the acidic gas removal device according to any one of the third to ninth inventions, in which a rich and lean solution heat exchanger exchanging heat between the leans solution and a rich solution is provided in the lean solution supply line, and the electric conductivity measurement means of the degradant concentration measurement device is provided between the heat exchanger and the absorption tower in the lean solution supply line.

An eleventh invention is the acidic gas removal device according to any one of the third to tenth inventions, in which an absorbing solution tank for storing the lean solution is provided in the lean solution supply line, and the degradant concentration measurement device is provided in the absorbing solution tank.

Advantageous Effects of Invention

According to the invention, since it is possible to obtain the concentration of the degradant contained in the acidic gas-absorbing solution from the measured electric conductivity of the acidic gas-absorbing solution, it is possible to reduce the burden of measuring the concentration of the degradant of the acidic gas-absorbing solution, and to efficiently and easily measure the concentration of the degradant in the acidic gas-absorbing solution. Then, since the concentration of the degradant in the acidic gas-absorbing solution is rapidly obtained, it is possible to take a rapid action so that the concentration of the degradant in the acidic gas-absorbing solution becomes equal to or less than the prescribed value.

BRIEF DESCRIPTION OF DRAWINGS

FIG. 6 is a flowchart illustrating an example of the control method in a case in which the reclaimer is operated in a continuous manner.

DESCRIPTION OF EMBODIMENTS

Hereinafter, the invention will be described in detail with reference to the accompanying drawings. Meanwhile, the invention is not limited to the following embodiment for carrying out the invention (hereinafter, referred to as embodiment). In addition, in the following embodiment, a configuration element includes an element that can be easily conceived by a person skilled in the art, a substantially identical element, and all elements belonging to an equivalent range thereof. Furthermore, configuration elements disclosed in the following embodiment can be combined as appropriate.

Figure 1:
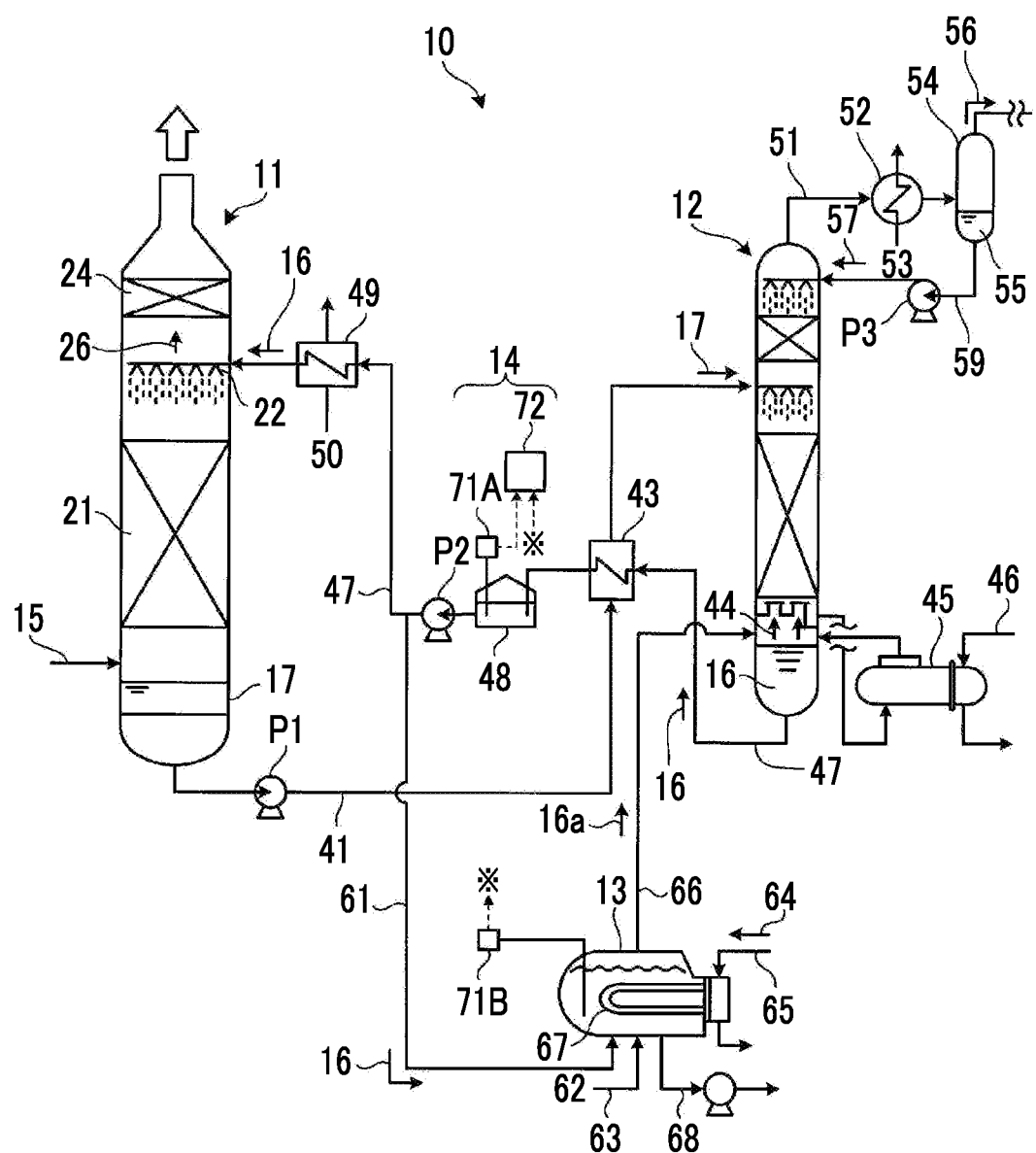
FIG. 1 is a schematic view illustrating a $CO_2$ recovery device to which a degradant concentration measurement device according to an embodiment of the invention is applied.

A degradant concentration measurement device according to a first embodiment of the invention will be described with reference to the accompanying drawings. FIG. 1 is a schematic view illustrating an acidic gas recovery device to which a degradant concentration measurement device according to a first embodiment of the invention is applied. As illustrated in FIG. 1, an acidic gas recovery device 10 has an acidic gas-absorbing tower (hereinafter referred to as absorption tower) 11, an absorbing solution-regeneration tower (hereinafter referred to as regeneration tower) 12, a reclaimer 13 and a degradant concentration measurement device 14.

The acidic gas recovery device 10 includes a circulation system in which an acidic gas-absorbing solution (hereinafter, also referred to as lean solution) absorbing an acidic gas component in supply gas to acidic gas removal device 15 is circulated between the absorption tower 11 and the regeneration tower 12 (hereinafter referred to as in the system), and a degradant removal system removing a degradant contained in the acidic gas-absorbing solution 16 by making the acidic gas-absorbing solution 16 be used after circulation in the circulation system. The circulation system includes an acidic gas component-absorbing system absorbing the acidic gas component in the absorption tower 11 and an acidic gas recovery and acidic gas-absorbing solution recycling system carrying out the recovery of the acidic gas component in the regeneration tower 12 and the regeneration of the acidic gas-absorbing solution 16.

In the acidic gas recovery device 10, the acidic gas-absorbing solution 16 is circulated in the system. The acidic gas-absorbing solution (lean solution) 16 is supplied to the absorption tower 11. In addition, an acidic gas-absorbing solution (rich solution) 17 having absorbed the acidic gas component in the supply gas to acidic gas removal device 15 is supplied to the regeneration tower 12 from the absorption tower 11. The acidic gas-absorbing solution (lean solution) 16 regenerated from the rich solution 17 by removing almost all the acidic gas component in the regeneration tower 12 is supplied to the absorption tower 11 from the regeneration tower 12.

The acidic gas-absorbing solution 16 used in the embodiment is not particularly limited as long as the acidic gas-absorbing solution is an absorbing solution used to purify supplied gas by being brought into contact with acidic gas including an acidic component and an oxidizing component, and examples of the acidic gas-absorbing solution 16 include alkanolamine, hindered amines having an alcoholic hydroxyl group, and the like that have been used in a gas purification step of a petroleum purification process or the like. Specific examples of the alkanolamine include monoethanolamine (MEA), diethanolamine (DEA), triethanolamine (TEA), diglycolamine (DGA), methyldiethanolamine (MDEA), diisopropanolamine (DIPA), and the like, and may be other amines. Generally, MEA is preferably used as the acidic gas-absorbing solution 16. In addition, examples of the hindered amines having an alcoholic hydroxyl group include 2-amino-2-methyl-1-propanol (AMP), 2-(ethylamino)-ethanol (EAE), 2-(methylamino)-ethanol (MAE), and the like.

The supply gas to acidic gas removal device 15 refers to gas containing acidic gas such as $CO_2$ exhausted from a boiler, a gas turbine or the like; $CO_2$ contained in coal gasified gas, synthetic gas, coke-oven gas, petroleum gas and natural gas; or gas containing an acidic gas such as $H_2S$. The supply gas to acidic gas removal device 15 is pressurized using an air blower, a compressor or the like, and is sent to the absorption tower 11.

The absorption tower 11 is a tower in which the supply gas to acidic gas removal device 15 and the acidic gas-absorbing solution 16 are brought into contact with each other, thereby removing acidic gas from the supply gas to acidic gas removal device 15. The absorption tower 11 has an acidic gas-absorbing section 21 and a demister 24. The supply gas to acidic gas removal device 15 supplied into the tower flows from the tower bottom section side to the tower top side.

The supply gas to acidic gas removal device 15 rising in the tower comes into countercurrent contact with the acidic gas-absorbing solution 16 containing, for example, a basic amine compound as the base at the acidic gas-absorbing section 21, and the acidic gas component in the supply gas to acidic gas removal device 15 is absorbed in the acidic gas-absorbing solution 16.

The acidic gas component in the supply gas to acidic gas removal device 15 is absorbed in the acidic gas-absorbing section 21 by spraying the acidic gas-absorbing solution 16 from a spraying nozzle 22, thereby turning the acidic gas-absorbing solution into the rich solution 17, and the rich solution is made to pass through the acidic gas-absorbing section 21 and then is stored in the tower bottom section. In addition, acidic gas-removed exhaust gas 26 obtained by removing the acidic gas component in the supply gas to acidic gas removal device 15 in the acidic gas-absorbing section 21 is made to pass through the demister 24, and is exhausted from the absorption tower 11.

In addition, in the embodiment, a single step of the acidic gas-absorbing section 21 is provided in the absorption tower 11, but the embodiment is not limited thereto, and multiple steps of the acidic gas-absorbing section may be provided.

The rich solution 17 having absorbed the acidic gas component in the supply gas to acidic gas removal device 15 at the acidic gas-absorbing section 21 is stored in the bottom section of the absorption tower 11. The rich solution 17 stored in the bottom section of the absorption tower 11 is extracted through a rich solution supply line 41, is sent by pressure using a pump P1 provided outside the top bottom section of the absorption tower 11, exchanges heat with the acidic gas-absorbing solution 16 regenerated in the regeneration tower 12 in a rich and lean solution heat exchanger 43, and is supplied into the tower from the tower top section of the regeneration tower 12.

The kind of the heat exchanger such as the rich and lean solution heat exchanger 43 used in the embodiment is not particularly limited, and, for example, a well-known heat exchanger such as a plate heat exchanger or a shell & tube heat exchanger may be used.

The regeneration tower 12 is a tower in which the acidic gas is emitted from the rich solution 17, thereby regenerating the rich solution as the lean solution 16. The rich solution 17 emitted from the tower top section of the regeneration tower 12 into the regeneration tower 12 is heated by vapor (steam) 44 supplied from the tower bottom section of the regeneration tower 12. The steam 44 is generated by exchanging heat between the lean solution and saturated steam 46 in a regeneration heater (reboiler) 45. The rich solution 17 having absorbed the acidic component and the oxidizing component in the absorption tower 11 is heated by the steam 44 in the regeneration tower 12, thereby thermally decomposing a thermally-decomposable amine salt such as an amine salt in the acidic gas. A majority of air diffusible acidic gas such as $CO_2$ contained in the rich solution 17 is emitted so that the rich solution 17 turns into the acidic gas-absorbing solution (lean solution) 16 from which the majority of air diffusible acidic gas such as almost all $CO_2$ contained in the solution has been removed when the rich solution 17 arrives at the tower bottom section of the regeneration tower 12.

The lean solution 16 stored in the bottom section of the regeneration tower 12 is extracted as the acidic gas-absorbing solution from the bottom section of the regeneration tower 12 through the lean solution supply line 47, exchanges heat with the rich solution 17 in the rich and lean solution heat exchanger 43, and then is sent to an absorbing solution tank 48.

The absorbing solution tank 48 is a tank provided in the lean solution supply line 47 to store the lean solution 16. The lean solution 16 is stored in the absorbing solution tank 48.

Meanwhile, in the embodiment, the absorbing solution tank 48 is provided on the rear side of the rich and lean solution heat exchanger 43, but the location is not limited thereto, and the absorbing solution tank may be provided on the front side of the rich and lean solution heat exchanger 43.

The lean solution 16 stored in the absorbing solution tank 48 is sent to a cooler 49 through the lean solution supply line 47 using a pump P2, exchanges heat with cooling water 50 in the cooler 49, and then is sent to the absorption tower 11.

Meanwhile, gas 51 accompanying water vapor is emitted from the tower top section of the regeneration tower 12. The gas 51 accompanying water vapor is derived from the tower top section of the regeneration tower 12, the water vapor contained in the gas 51 is condensed using cooling water 53 in a condenser 52, and water 55 is separated in a separation drum 54. An acidic gas component 56 separated from the water 55 in the separation drum 54 is sent to a treatment system. In addition, the water 55 separated in the separation drum 54 is supplied as refluxed water 57 to the top section of the regeneration tower 12 through a refluxed water supply line 59 using a pump P3.

In addition, a lean solution branching line 61 is provided in the lean solution supply line 47, and some of the lean solution 16 sent to the absorption tower 11 from the absorbing solution tank 48 is extracted. The lean solution 16 sent to the absorption tower 11 is extracted to the lean solution branching line 61, and is supplied to the reclaimer 13.

The reclaimer 13 removes a concentrated waste generated by separating by distillation or separating by distillation under reduced pressure a degradant such as a salt remaining in the lean solution 16 generated in the regeneration tower 12 using the boiling point difference. The reclaimer 13 is a distillation-type reclaimer separating a degradant using the difference in the boiling point between the degradant and the absorbing solution. In addition, water 62 is supplied to the reclaimer 13 through a water supply line 63, and saturated steam 64 is supplied to the reclaimer 13 through a saturated steam supply line 65. The lean solution 16 and the water 62 are heated in the reclaimer 13 using the saturated steam 64 supplied from the saturated steam supply line 65, whereby the lean solution 16 is gasified. A gasified acidic gas-absorbing solution 16a is supplied to the tower bottom section of the regeneration tower 12 through a gasified acidic gas-absorbing solution supply line 66.

The gasified acidic gas-absorbing solution 16a may be cooled in a condenser, be liquefied by condensation, and be returned to the absorbing solution tank 48.

In the embodiment, the degradant refers to a degradant generated from a reaction with an amine-based absorbing solution when removing the acidic gas component from the supply gas to acidic gas removal device 15 in the absorption tower 11, and examples thereof include heat stable amine salts (HSAS) such as amine salts of non-air diffusible acidic components such as formic acid, acetic acid, propionic acid, oxalic acid, malonic acid, fumaric acid, glycolic acid, lactic acid, thiocyanic acid, hydrochloric acid, thiosulfuric acid, sulfurous acid and other inorganic acids; oxides of an amine such as visine; other denatures thereof; and the like.

The heat stable amine salts (HSAS) such as amine salts of non-air diffusible acidic components, oxides of an amine such as visine and other denatures thereof are not decomposed in the regeneration tower 12, and are circulated in the absorption tower 11 in a state of being accumulated in the lean solution 16. When the heat stable amine salt (HSAS) is accumulated in the lean solution 16, the absorption efficiency of the lean solution 16 in the absorption tower 11 decreases, and the corrosion of the devices is caused, and therefore the heat stable amine salt is removed in the reclaimer 13 when the concentration of the degradant in the lean solution 16 reaches a predetermined concentration.

The lean solution 16 supplied to the reclaimer 13 is heated using the saturated steam 64 supplied from the saturated steam supply line 65 in the reclaimer 13 through a steam supply tube 67 in the reclaimer 13, whereby the degradant is removed.

The gasified acidic gas-absorbing solution 16a gasified in the reclaimer 13 is supplied, together with the steam, to the tower bottom section of the regeneration tower 12 through the gasified acidic gas-absorbing solution supply line 66. The gasified acidic gas-absorbing solution 16a may be cooled in the condenser, be liquefied by condensation, and be returned to the absorbing solution tank 48.

In addition, when the lean solution 16 is heated, the degradant in the lean solution 16 is condensed in an inner bottom section of the reclaimer 13. This heated and condensed degradant is exhausted from the reclaimer 13, is moved to a treatment tank, not illustrated, through a waste exhaustion line 68 and a tank lorry or the like, not illustrated, or is temporarily stored in a storage tank, is sent to a waste incinerator, and is treated.

In addition, in the embodiment, only the reclaimer 13 is used for the removal of the degradant such as a salt remaining in the lean solution 16, but a device is not limited thereto, and a device in which any one of a distillation under reduced pressure method, an ion-exchange resin method and an electrodialysis method is used may be used instead of the reclaimer 13, or a device in which any one of a distillation under reduced pressure method, an ion-exchange resin method and an electrodialysis method is used may be jointly used with the reclaimer 13. The device in which the distillation under reduced pressure method is used is a device in which a degradant is removed by heating from the lean solution 16 on a thin film using multiple steps of a thin film evaporator. The device in which the ion-exchange resin method is used is a device in which a degradant is separated using an ion-exchange resin selectively adsorbing an ionized degradant. The device in which the electrodialysis method is used is a device in which a degradant is separated using a selective membrane selectively permeating an ionized degradant. When any one or more of the devices in which any one of a distillation under reduced pressure method, an ion-exchange resin method and an electrodialysis method is used are jointly used in addition to the reclaimer 13, it is possible to more effectively remove the degradant remaining in the lean solution 16.

In addition, in the embodiment, some of the lean solution 16 is extracted at a location between the rich and lean solution heat exchanger 43 and the cooler 49 in the lean solution branching line 61, but the location is not limited thereto, and some of the lean solution may be extracted on the front side of the rich and lean solution heat exchanger 43 or on the rear side of the cooler 49.

(Degradant Concentration Measurement Device)

The degradant concentration measurement device 14 has electric conductivity measurement instruments (electric conductivity measurement means) 71A and 71B and a detection device (detection means) 72. The electric conductivity measurement instruments 71A and 71B measure the electric conductivity of the lean solution 16 that absorbs the acidic gas component contained in the supply gas to acidic gas removal device 15, then, is regenerated, circulated again and used. The electric conductivity measurement instrument 71A is provided in the absorbing solution tank 48, and the electric conductivity measurement instrument 71B is provided in the reclaimer 13. The marks 1 and 2 mean that there is an omission of a line connecting between the element 71 B and the element 72.

The detection device 72 obtains the concentration of the degradant contained in the lean solution 16 from the measured electric conductivity of the lean solution 16 based on the relationship between the previously-obtained electric conductivity of the lean solution 16 that is the acidic gas-absorbing solution and the concentration of the degradant. In addition, a control device (not illustrated) controls at least any one of starting and stopping of the operation of the reclaimer 13 and the supply flow rate of the lean solution 16 supplied to the reclaimer 13 based on the electric conductivity of the lean solution 16 measured in the detection device 72.

Figure 2:
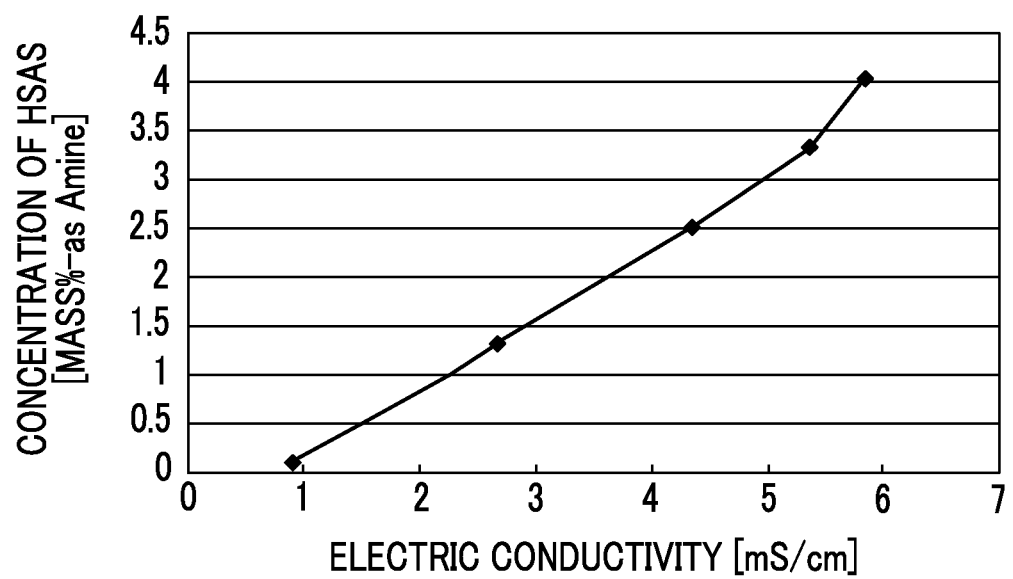
FIG. 2 is a view illustrating the actual measurement results of an electric conductivity of a lean solution and a concentration of a heat stable salt.

To help the understanding of the relationship between the electric conductivity and the concentration of the degradant, the results of the electric conductivity of the lean solution 16 extracted from the acidic gas recovery device 10 and the concentration of the heat stable amine salt (HSAS) actually measured using an electric conductivity meter (Serial No. HI 98130/Combo 2) manufactured by Hanna Instruments are illustrated in FIG. 2. Meanwhile, the measurement temperature condition was set in a range of 14° C. to 17° C. As illustrated in FIG. 2, there is a tendency of the concentration of the degradant to increase as the electric conductivity of the lean solution 16 increases. Since there is a correlation as illustrated in FIG. 2 between the electric conductivity of the lean solution 16 and the concentration of the degradant, it is possible to estimate the concentration of the degradant in the lean solution 16 by measuring the electric conductivity of the lean solution 16. Therefore, in a case in which the electric conductivity of the lean solution 16 reaches a predetermined prescribed value, it is possible to easily specify a value corresponding to the management value of the concentration of the degradant. Meanwhile, while the electric conductivity of the lean solution 16 slightly changes depending on the composition of the degradant, the concentration of the degradant increases as the electric conductivity increases, and the same tendency appears.

Therefore, in the degradant concentration measurement device 14, it is possible to obtain the concentration of the degradant contained in the lean solution 16 using the detection device 72 from the electric conductivity of the lean solution 16 measured in the electric conductivity measurement instrument 71A based on the relationship diagram between the electric conductivity and the concentration of the degradant as illustrated in FIG. 2.

In addition, as an example in which the electric conductivity is used as an index for operation management, there has been an example in which the regeneration timing of an ion-exchange resin is used as an index as described in PTL 2, but this example is different from the idea of the embodiment in which the degradant concentration measurement device 14 controls the operation of the reclaimer 13 and the supply flow rate of the lean solution based on the relationship between the electric conductivity of the lean solution 16 and the concentration of the degradant.

Therefore, since it is possible to obtain the concentration of the degradant contained in the lean solution 16 from the measured electric conductivity of the lean solution 16 when the degradant concentration measurement device 14 is used, it is possible to reduce the burden of measuring the concentration of the degradant in the lean solution 16 and to efficiently and easily measure the concentration of the degradant in the lean solution 16. That is, when the degradant concentration measurement device 14 is used, since it is not necessary for an operator to measure the concentration of the degradant in the lean solution 16 and to determine whether or not the concentration of the degradant exceeds the management value unlike the related art, it is possible to reduce the burden of the operator for the measurement of the concentration of the degradant and the determination. In addition, since the concentration of the degradant contained in the lean solution 16 is automatically obtained from the electric conductivity of the lean solution 16, the efficiency of the measurement of the concentration of the degradant in the lean solution 16 improves, and it is possible to easily measure the concentration of the degradant in the lean solution 16.

Then, since the concentration of the degradant in the lean solution 16 can be automatically and rapidly obtained, in a case in which the electric conductivity of the lean solution 16 circulating in the circulation system is more than the prescribed value, it is possible to easily determine that the concentration of the degradant in the lean solution 16 exceeds the prescribed value, and therefore, it is possible to take a rapid action so as to make the concentration of the degradant in the lean solution 16 equal to or less than the prescribed value by extracting the lean solution 16 into the lean solution branching line 61, supplying the lean solution to the reclaimer 13, and carrying out a removal operation of the degradant in the lean solution 16 circulating in the circulation system.

In addition, generally, the sizes of the devices become larger to analyze the concentration of the degradant such as HSAS, and the cost burden is likely to increase. On the contrary, since the degradant concentration measurement device 14 measures the concentration of the degradant using the electric conductivity measurement instrument 71A, it is possible to easily move the measurement place, and to repeatedly and continuously use the degradant concentration measurement device at a low cost, and therefore it is possible to reduce the cost burden necessary to measure the concentration of the degradant.

In addition, regarding the measurement of the electric conductivity, since it is preferable to measure the electric conductivity of the lean solution 16 in an ordinary-temperature-and-pressure state before the absorption of the acid gas component contained in the supply gas to acidic gas removal device 15, in the embodiment, the electric conductivity measurement instrument 71A is provided in the absorbing solution tank 48. In addition, in a case in which the absorbing solution tank 48 is not in an ordinary-temperature-and-pressure state, it is desirable to put the absorbing solution tank 48 in an ordinary-temperature-and-pressure state through heat exchange or pressure adjustment. In addition, the installation place of the electric conductivity measurement instrument 71A is not limited thereto, and the electric conductivity measurement instrument may be installed at any location at which the electric conductivity of the lean solution 16 in the circulation system can be measured, and the electric conductivity measurement instrument may be installed at, for example, between the absorbing solution tank 48 and the cooler 49, between the cooler 49 and the absorption tower 11, or in the reboiler 45.

The detection device 72 is capable of obtaining the concentration of the degradant contained in the lean solution 16 from the electric conductivity of the lean solution 16 measured in the electric conductivity measurement instrument 71A based on the relationship between the previously-obtained electric conductivity of the lean solution 16 and the concentration of the degradant. Therefore, the control device (not illustrated) preferably controls the starting and stopping of the operation of the reclaimer 13 and the supply flow rate of the lean solution 16 to the reclaimer 13 based on the electric conductivity of the lean solution 16 measured in the electric conductivity measurement instrument 71A in the degradant concentration measurement device 14.

When the electric conductivity of the lean solution measured in the electric conductivity measurement instrument 71A is in a range of 1 mS/cm to 30 mS/cm, it is preferable to operate the reclaimer 13. This is considered to be because it is necessary to suppress the degradant contained in the lean solution 16 in a range of 1 mass % to 3 mass % as Amine, and the electric conductivity corresponding to the concentration of the degradant contained in the lean solution 16 in a range of 1 mass % to 3 mass % as Amine is in a range of 1 mS/cm to 30 mS/cm.

In addition, since the degradant concentration measurement device 14 has the electric conductivity measurement instrument 71B, the control device (not illustrated) may be allowed to control the starting and stopping of the operation of the reclaimer 13 and the supply flow rate of the lean solution 16 to the reclaimer by measuring the electric conductivity of the lean solution 16 supplied to the reclaimer 13 using the electric conductivity measurement instrument 71A.

Figure 3:
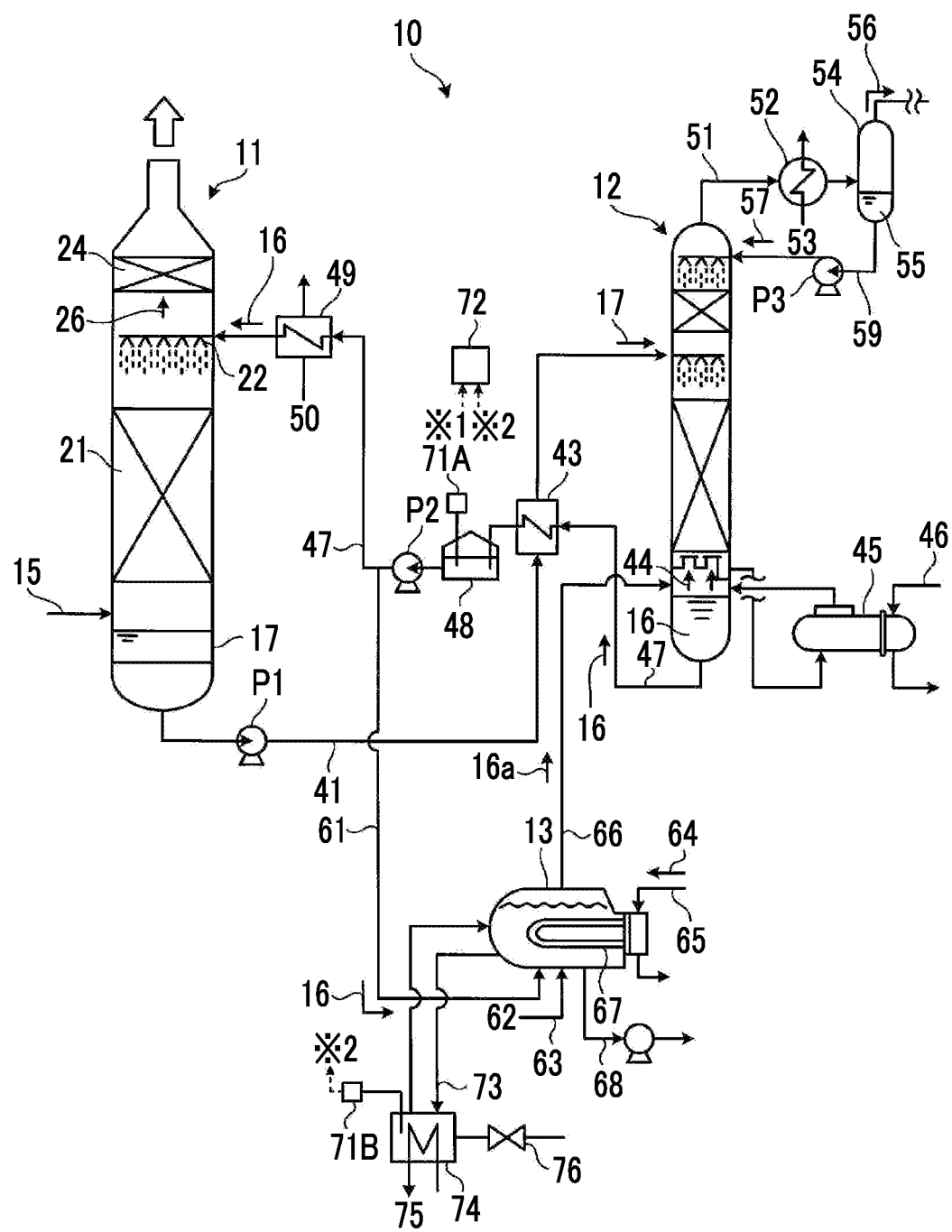
FIG. 3 is a view illustrating another configuration of an acidic gas recovery device.

In addition, in the embodiment, the degradant concentration measurement device 14 measures the lean solution 16 in the reclaimer 13, but the measured lean solution 16 is not limited thereto, and some of the lean solution 16 in the reclaimer 13 may be extracted and measured. FIG. 3 is a view illustrating another configuration of the acidic gas recovery device 10. As illustrated in FIG. 3, the acidic gas recovery device 10 has a lean solution extraction line 73 extracting some of the lean solution 16 in the reclaimer 13 and a cooling device 74 cooling the lean solution 16. The cooling device 74 is provided in the lean solution extraction line 73, and the degradant concentration measurement device 14 is provided in the cooling device 74. The lean solution 16 in the reclaimer 13 is sent to the cooling device 74 through the lean solution extraction line 73, and is cooled using cooling water 75. In addition, in a case in which the lean solution 16 is not at an ordinary pressure, the pressure is adjusted using a pressure adjustment valve 76. The degradant concentration measurement device 14 (refer to FIG. 1) measures the lean solution 16 in the cooling device 74 under an ordinary-temperature-and-pressure condition. The lean solution 16 in the cooling device 74 is used for the measurement of the lean solution in the degradant concentration measurement device 14 (refer to FIG. 1), and then, again, is sent to the reclaimer 13 through the lean solution extraction line 73. Then, it is possible to stably measure the electric conductivity of the lean solution 16 in the reclaimer 13.

In addition, the operation of measuring the electric conductivity at an ordinary temperature and an ordinary pressure after extracting some of the lean solution 16 and adjusting the temperature and the pressure is not limited to lean solution 16 in the reclaimer 13, and can also be applied to the lean solution 16 and the like in the absorbing solution tank 48.

(Method for Controlling the Operation of the Reclaimer 13 Using the Degradant Concentration Measurement Device 14)

Next, a method for controlling the operation of the reclaimer 13 using the degradant concentration measurement device 14 according to the embodiment will be described. Meanwhile, the starting and stopping of the operation of the reclaimer 13 and the supply flow rate of the lean solution 16 supplied to the reclaimer 13 are controlled using the control device (not illustrated).

Figure 4:
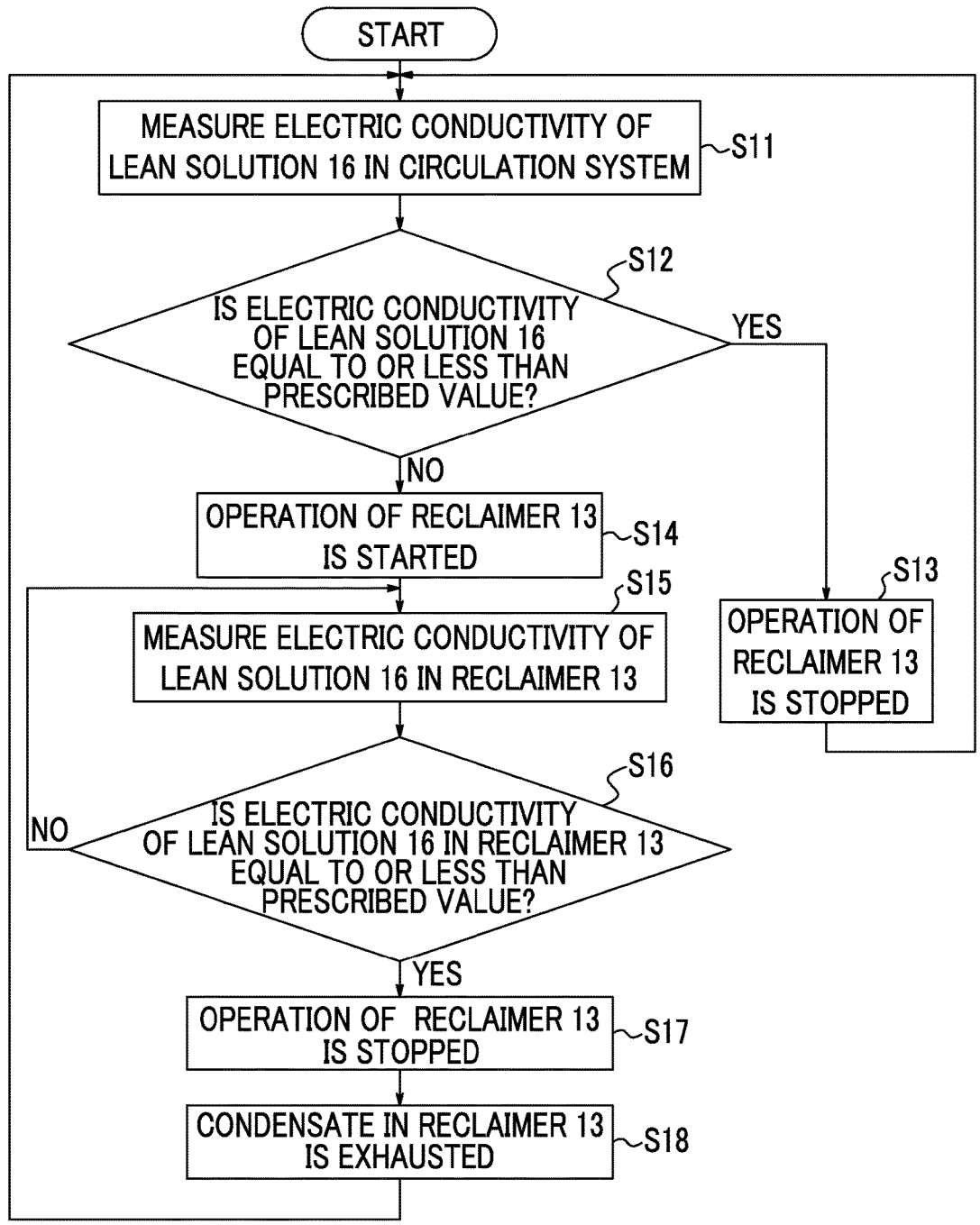
FIG. 4 is a flowchart illustrating an example of a control method in a case in which a reclaimer is operated in a semi-batch manner.

FIG. 4 is a flowchart illustrating an example of a control method in a case in which the reclaimer 13 is operated in a semi-batch manner. As illustrated in FIG. 4, the electric conductivity of the lean solution 16 in the circulation system is measured in the degradant concentration measurement device 14 (Step S11), and whether or not the electric conductivity of the lean solution 16 is equal to or less than the prescribed value (for example, 2.5 mS/cm) is determined (Step S12).

In a case in which the electric conductivity of the lean solution 16 is 2.5 mS/cm, the electric conductivity corresponds to the concentration of the degradant of 1.2 mass % as Amine. Therefore, in a case in which the electric conductivity of the lean solution 16 is determined to be equal to or less than the prescribed value (for example, 2.5 mS/cm) (Step S12: Yes), the reclaimer 13 is left to be idle (Step S13), and the electric conductivity of the lean solution 16 in the circulation system is measured again in the degradant concentration measurement device 14 after a predetermined period of time elapses.

In a case in which the electric conductivity of the lean solution 16 is determined to be more than the prescribed value (for example, 2.5 mS/cm) (Step S12: No), the operation of the reclaimer 13 is started (Step S14). After that, the electric conductivity of the lean solution 16 supplied to the reclaimer 13 is measured (Step S15), and whether or not the electric conductivity of the lean solution 16 in the reclaimer 13 is equal to or more than the prescribed value (for example, 40 mS/cm) is determined (Step S16).

In a case in which the electric conductivity of the lean solution 16 is 40 mS/cm, the electric conductivity corresponds to the concentration of the degradant of approximately 30 mass % as Amine. In a case in which the electric conductivity of the lean solution 16 in the reclaimer 13 is determined to be less than the prescribed value (for example, 40 mS/cm) (Step S16: No), the electric conductivity of the lean solution 16 in the reclaimer 13 is measured again after a predetermined period of time elapses.

In a case in which the electric conductivity of the lean solution 16 in the reclaimer 13 is determined to be equal to or more than the prescribed value (for example, 40 mS/cm) (Step S16: No), the operation of the reclaimer is stopped (Step S17), and the condensate in the reclaimer 13 is exhausted (Step S18).

After the exhaustion of the condensate in the reclaimer 13, the electric conductivity of the lean solution 16 in the circulation system measured in the degradant concentration measurement device 14 is measured again.

The changes in the electric conductivities of the lean solution 16 in the circulation system and the lean solution 16 in the reclaimer 13 when the operation of the reclaimer 13 is controlled using the method for controlling the operation of the reclaimer 13 using the degradant concentration measurement device 14 according to the embodiment will be described.

Figure 5:
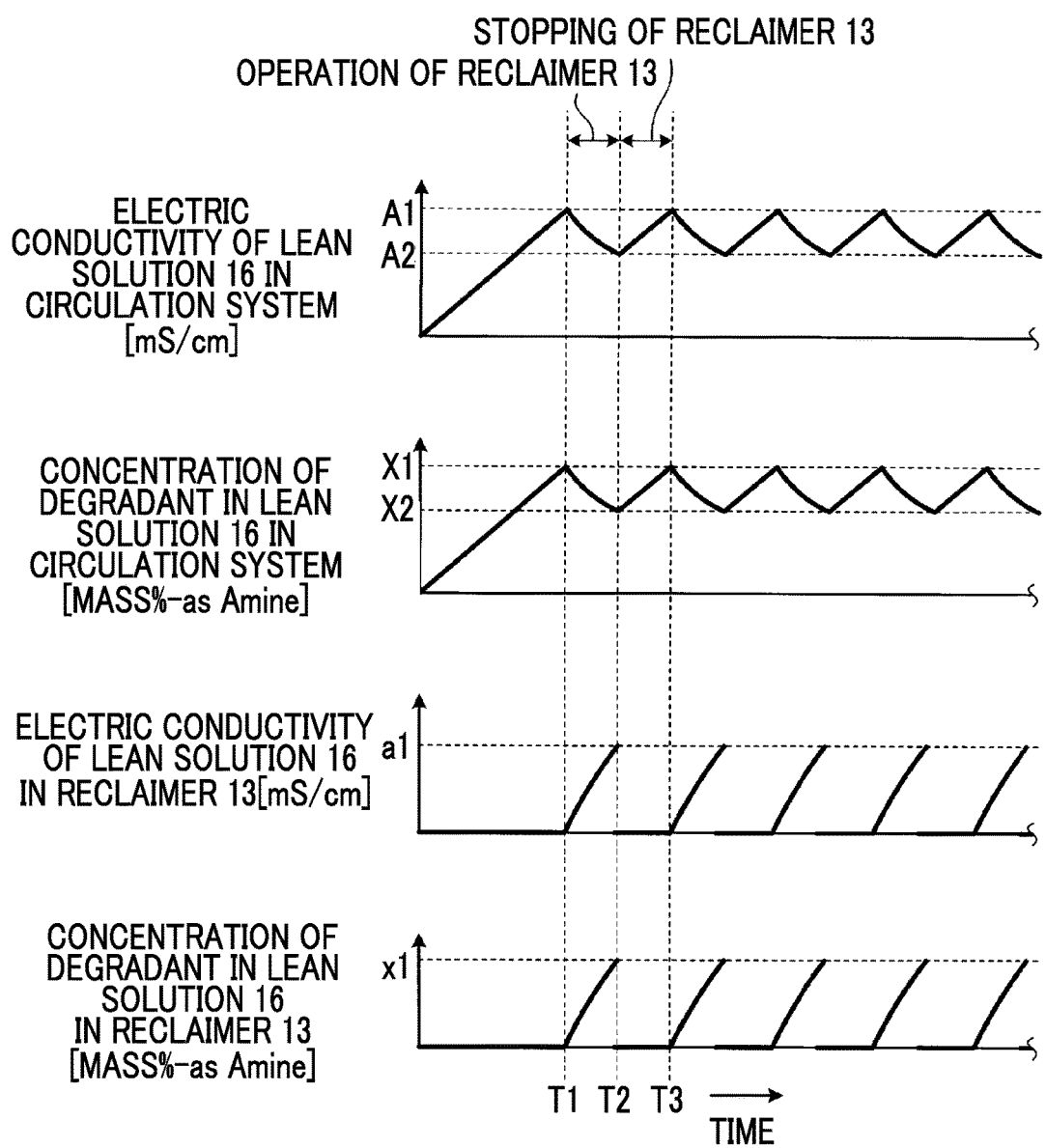
FIG. 5 is a view illustrating examples of changes in the electric conductivity of the lean solution in a circulation system and the concentration of a degradant in the system in a case in which the reclaimer is operated in a semi-batch manner.

FIG. 5 is a view illustrating an example of the change in the electric conductivity of the lean solution 16 in the circulation system and the concentration of the degradant in the system. When the electric conductivity of the lean solution 16 circulating between the absorption tower 11 and the regeneration tower 12 in the system reaches a management value A1 (for example, 2.5 mS/cm) at a point in time T1 at which a predetermined period of time has elapsed from the starting of the operation of the acidic gas recovery device 10 as illustrated in FIG. 5, the concentration of the degradant in the lean solution 16 in the circulation system is determined to correspond to a standard value X1 (for example, 1.2 mass % as Amine), and the operation of the reclaimer 13 is automatically started.

At this time, the electric conductivity of the lean solution 16 in the reclaimer 13 and the concentration of the degradant continuously increase, the electric conductivity of the lean solution 16 in the reclaimer 13 reaches a predetermined value A1 (for example, 40 mS/cm) at a point in time T2 at which a predetermined period of time has elapsed from the starting of the operation of the acidic gas recovery device 10, the concentration of the degradant in the reclaimer 13 is determined to correspond to a predetermined value X1 (for example, 30 mass % as Amine), and the operation of the reclaimer 13 is automatically stopped. At this time, the electric conductivity of the lean solution 16 in the circulation system decreases up to a predetermined value A2 (for example, 1.9 mS/cm), and the concentration of the degradant in the lean solution 16 is determined to decrease up to a predetermined value X2 (for example, 0.8 mass %).

While the reclaimer 13 is not in operation, the lean solution 16 and the degradant in the reclaimer 13 are separated from each other, and the degradant is exhausted from the reclaimer 13.

After that, when the electric conductivity of the lean solution 16 in the circulation system reaches the management value A1 (for example, 2.5 mS/cm) again at a point in time T3 at which a predetermined period of time has elapsed from the starting of the operation, the concentration of the degradant in the lean solution 16 in the circulation system is determined to correspond to the standard value X1 (for example, 1.2 mass % as Amine), and the operation of the reclaimer 13 is automatically started.

As described above, since the concentration of the degradant in the lean solution 16 is obtained depending on the electric conductivity of the lean solution 16 in the circulation system measured in the degradant concentration measurement device 14, it is possible to control the operation of the reclaimer 13. Therefore, it is possible to remove the degradant in the lean solution 16 in the reclaimer 13 depending on the concentration of the degradant in the lean solution 16 in the circulation system, and to reduce the concentration of the degradant in the lean solution 16 in the circulation system to be less than the management value. Therefore, it is possible to appropriately operate the reclaimer 13 by controlling the operation of the reclaimer 13 using the degradant concentration measurement device 14 according to the embodiment, and therefore it is possible to remove the degradant in the lean solution 16 and take a rapid action to make the concentration of the degradant in the lean solution 16 equal to or less than the prescribed value, and it is also possible to reduce the cost for measuring the concentration of the heat stable amine salt (HSAS) in the lean solution 16 and the cost for operating the reclaimer 13.

While the control method in a case in which the reclaimer 13 is operated in a semi-batch manner has been described in FIG. 4, the control method is not limited thereto, and the operation of the reclaimer 13 may be controlled in the same manner using the degradant concentration measurement device 14 according to the embodiment even in a case in which the reclaimer 13 is operated in a continuous manner.

FIG. 6 is a flowchart illustrating an example of a control method in a case in which the reclaimer 13 is operated in a continuous manner. As illustrated in FIG. 6, the electric conductivity of the lean solution 16 in the circulation system measured in the degradant concentration measurement device 14 is measured (Step S21), and whether or not the electric conductivity of the lean solution 16 is equal to or less than the prescribed value (for example, 2.5 mS/cm) is determined (Step S22).

In a case in which the electric conductivity of the lean solution 16 is determined to be equal to or less than the prescribed value (for example, 2.5 mS/cm) (Step S22: Yes), the reclaimer 13 is left to be idle (Step S23), and the electric conductivity of the lean solution 16 in the circulation system is measured again in the degradant concentration measurement device 14 after a predetermined period of time elapses.

In a case in which the electric conductivity of the lean solution 16 is determined to be more than the prescribed value (for example, 2.5 mS/cm) (Step S22: No), the operation of the reclaimer 13 is started (Step S24).

After that, the electric conductivity of the lean solution 16 in the circulation system is measured (Step S25), and whether or not the electric conductivity of the lean solution 16 in the circulation system has a decreasing tendency is determined (Step S26). In a case in which the electric conductivity of the lean solution 16 in the circulation system has a decreasing tendency (Step S26: Yes), a control is carried out to decrease the supply flow rate of the lean solution 16 supplied to the reclaimer 13 (Step S27). In addition, in a case in which the electric conductivity of the lean solution 16 in the circulation system has an increasing tendency (Step S26: No), a control is carried out to increase the supply flow rate of the lean solution 16 supplied to the reclaimer 13 (Step S28). With the above-described controls, the reclaimer 13 is operated to maintain the electric conductivity of the lean solution 16 in the circulation system at the prescribed value.

Therefore, even in a case in which the reclaimer 13 is operated in a continuous manner, it is possible to remove the degradant in the lean solution 16 in the reclaimer 13 depending on the concentration of the degradant in the lean solution 16 in the circulation system and to reduce the concentration of the degradant in the lean solution 16 in the circulation system to be less than the management value by controlling the operation of the reclaimer 13 based on the electric conductivity of the lean solution 16 in the circulation system measured in the degradant concentration measurement device 14 using the degradant concentration measurement device 14 according to the embodiment. Therefore, it is possible to appropriately operate the reclaimer 13 by controlling the operation in a continuous manner using the degradant concentration measurement device 14 according to the embodiment, and therefore it is possible to remove the degradant in the lean solution 16 and take a rapid action to make the concentration of the degradant in the lean solution 16 equal to or less than the prescribed value, and it is also possible to reduce the cost for measuring the concentration of the heat stable amine salt (HSAS) in the lean solution 16 and the cost for operating the reclaimer 13.

Therefore, according to the acidic gas recovery device 10 to which the degradant concentration measurement device 14 according to the embodiment is applied, it is possible to efficiently recover the degradant in the lean solution 16 and to improve the operation efficiency of the entire device.

Meanwhile, a case in which the degradant concentration measurement device 14 according to the embodiment is applied to the acidic gas recovery device 10 removing exhaust gas containing the acidic gas component exhausted from a boiler, a gas turbine or the like using the lean solution 16 has been described, but the invention is not limited thereto, and it is also possible to apply the invention in the same manner even in a case in which an acidic gas component contained in gas such as gasified gas, coal gasified gas, synthetic gas, coke-oven gas or natural gas generated when a fuel such as coal is gasified in a gasification furnace is removed as long as the acidic gas recovery device can be used to measure and manage a degradant contained in an absorbing solution used to remove acidic gas components (for example, $H_2S$, $CO_2$ and the like) contained in gas.

REFERENCE SIGNS LIST

10 ACIDIC GAS RECOVERY DEVICE
11 ACIDIC GAS ABSORBING TOWER (ABSORPTION TOWER)
12 ABSORBING SOLUTION-REGENERATION TOWER (REGENERATION TOWER)
13 RECLAIMER
14 DEGRADANT CONCENTRATION MEASUREMENT DEVICE
15 SUPPLY GAS TO ACIDIC GAS REMOVAL DEVICE
16 ACIDIC GAS-ABSORBING SOLUTION (LEAN SOLUTION)
16A GASIFIED ACIDIC GAS-ABSORBING SOLUTION
17 ACIDIC GAS-ABSORBING SOLUTION(RICH SOLUTION)
21 ACIDIC GAS-ABSORBING SECTION
22 SPRAYING NOZZLE
24 DEMISTER
26 ACIDIC GAS-REMOVED EXHAUST GAS
41 RICH SOLUTION SUPPLY LINE
43 RICH AND LEAN SOLUTION HEAT EXCHANGER
44 STEAM
45 REGENERATION HEATER (REBOILER)
46 SATURATED STEAM
47 LEAN SOLUTION SUPPLY LINE
48 ABSORBING SOLUTION TANK
49 COOLER
50, 53, 75 COOLING WATER
51 GAS
52 CONDENSER
54 SEPARATION DRUM
55 WATER
56 ACIDIC GAS COMPONENT
57 REFLUXED WATER
59 REFLUXED WATER SUPPLY LINE
61 LEAN SOLUTION BRANCHING LINE
62 WATER
63 WATER SUPPLY LINE
64 SATURATED STEAM
65 SATURATED STEAM SUPPLY LINE
66 GASIFIED ACIDIC GAS-ABSORBING SOLUTION SUPPLY LINE
67 STEAM SUPPLY TUBE
68 WASTE EXHAUSTION LINE
71A, 71B ELECTRIC CONDUCTIVITY MEASUREMENT INSTRUMENT (ELECTRIC CONDUCTIVITY MEASUREMENT MEANS)
72 DETECTION DEVICE
73 LEAN SOLUTION EXTRACTION LINE
74 COOLING DEVICE
P1 TO P3 PUMP

The invention claimed is:

1. An acidic gas removal device, comprising:
an absorption tower in which supply gas supplied to the acidic gas removal device and containing an acidic gas component is brought into contact with an acidic gas-absorbing solution so as to absorb and remove the acidic gas component;
an absorbing solution-regeneration tower in which the acidic gas-absorbing solution absorbing the acidic gas component in the absorption tower is regenerated so as to produce a lean solution; and
a degradant concentration measurement device comprising:
an electric conductivity measurement instrument for measuring an electric conductivity of the acidic gas-absorbing solution that absorbs the acidic gas component contained in the supply gas to the acidic gas removal device, then, is regenerated, circulated again and used; and
detection device for obtaining a concentration of degradant contained in the acidic gas-absorbing solution from the measured electric conductivity of the acidic gas-absorbing solution based on a previously obtained relationship between an electric conductivity of the acidic gas-absorbing solution and a concentration of the degradant contained in the acidic gas-absorbing solution,
wherein a lean solution supply line supplying the lean solution to the absorption tower from the absorbing solution-regeneration tower is provided, an electric conductivity of the lean solution is measured, and a concentration of a degradant is detected, and
wherein the acidic gas removal device further comprises:
a lean solution branching line that extracts some of the lean solution from the lean solution supply line; and a reclaimer that separates and removes a degradant in the lean solution extracted into the lean solution branching line by distillation using a boiling point difference.

2. The acidic gas removal device according to claim 1, wherein a rich and lean solution heat exchanger exchanging heat between the lean solution and a rich solution is provided in the lean solution supply line, and the electric conductivity measurement instrument of the degradant concentration measurement device is provided between the heat exchanger and the absorption tower in the lean solution supply line.

3. The acidic gas removal device according to claim 1, wherein an absorbing solution tank for storing the lean solution is provided in the lean solution supply line, and the degradant concentration measurement device is provided in the absorbing solution tank.

4. The acidic gas removal device according to claim 1, wherein a rich and lean solution heat exchanger exchanging heat between the lean solution and a rich solution is provided in the lean solution supply line, and the electric conductivity measurement instrument of the degradant concentration measurement device is provided between the heat exchanger and the absorption tower in the lean solution supply line.

5. The acidic gas removal device according to claim 1, comprising:

control means for controlling at least any one of starting and stopping of an operation of the reclaimer and a supply flow rate of the lean solution supplied to the reclaimer based on the electric conductivity of the lean solution measured in the degradant concentration measurement device.

6. The acidic gas removal device according to claim 5, wherein the control means starts the operation of the reclaimer in a case in which the electric conductivity of the lean solution measured in the degradant concentration measurement device is in a range of 1 mS/cm to 30 mS/cm.

7. The acidic gas removal device according to claim 5, wherein a rich and lean solution heat exchanger exchanging heat between the lean solution and a rich solution is provided in the lean solution supply line, and the electric conductivity measurement instrument of the degradant concentration measurement device is provided between the heat exchanger and the absorption tower in the lean solution supply line.

8. The acidic gas removal device according to claim 5, wherein the control means determines whether or not the electric conductivity of the lean solution measured in the degradant concentration measurement device is equal to or less than a prescribed value so as to determine whether or not to start the operation of the reclaimer, and, after the starting of the operation of the reclaimer, determines whether or not the electric conductivity of the lean solution in the reclaimer measured in the degradant concentration measurement device is equal to or more than the prescribed value so as to determine the operation of the reclaimer.

9. The acidic gas removal device according to claim 8, wherein the control means starts the operation of the reclaimer in a case in which the electric conductivity of the lean solution measured in the degradant concentration measurement device is in a range of 1 mS/cm to 30 mS/cm.

10. The acidic gas removal device according to claim 8, wherein a rich and lean solution heat exchanger exchanging heat between the lean solution and a rich solution is provided in the lean solution supply line, and the electric conductivity measurement instrument of the degradant concentration measurement device is provided between the heat exchanger and the absorption tower in the lean solution supply line.

11. The acidic gas removal device according to claim 5, wherein the control means determines whether or not the electric conductivity of the lean solution measured in the degradant concentration measurement device is equal to or less than a prescribed value so as to determine whether or not to start the operation of the reclaimer, and, after the starting of the operation of the reclaimer, determines whether or not the electric conductivity of the lean solution in the reclaimer measured in the degradant concentration measurement device has a decreasing tendency and adjusts the supply flow rate of the lean solution supplied to the reclaimer.

12. The acidic gas removal device according to claim 11, wherein the control means starts the operation of the reclaimer in a case in which the electric conductivity of the lean solution measured in the degradant concentration measurement device is in a range of 1 mS/cm to 30 mS/cm.

* * * * *